(12) United States Patent
Sant et al.

(10) Patent No.: US 10,932,890 B1
(45) Date of Patent: Mar. 2, 2021

(54) ENHANCED TECHNIQUES FOR DETERMINATION OF DENTAL MARGINS IN INTRAORAL SCANS

(71) Applicant: Pearl Inc., West Hollywood, CA (US)

(72) Inventors: Nishita Kailashnath Sant, Los Angeles, CA (US); Nandakishore Puttashamachar, Los Angeles, CA (US); Rohit Sanjay Annigeri, Los Angeles, CA (US); Cambron Neil Carter, Los Angeles, CA (US)

(73) Assignee: Pearl Inc., West Hollywood, CA (US)

( * ) Notice: Subject to any disclaimer, the term of this patent is extended or adjusted under 35 U.S.C. 154(b) by 0 days.

(21) Appl. No.: 16/684,427

(22) Filed: Nov. 14, 2019

(51) Int. Cl.
| | |
|---|---|
| *A61C 13/00* | (2006.01) |
| *G16H 50/20* | (2018.01) |
| *A61C 9/00* | (2006.01) |
| *G06T 15/08* | (2011.01) |
| *G16H 30/40* | (2018.01) |
| *G06T 17/20* | (2006.01) |

(52) U.S. Cl.
CPC ........ *A61C 13/0004* (2013.01); *A61C 9/0053* (2013.01); *G06T 15/08* (2013.01); *G06T 17/205* (2013.01); *G16H 30/40* (2018.01); *G16H 50/20* (2018.01); *G06T 2210/12* (2013.01); *G06T 2210/21* (2013.01); *G06T 2210/41* (2013.01)

(58) Field of Classification Search
CPC .. A61C 13/0004; A61C 9/0053; G16H 50/20; G16H 30/40; G06T 15/08; G06T 17/205; G06T 15/00
See application file for complete search history.

(56) References Cited

U.S. PATENT DOCUMENTS

| | | | |
|---|---|---|---|
| 5,417,572 A | 5/1995 | Kawai et al. | |
| 6,201,880 B1 | 3/2001 | Elbaum et al. | |
| 10,219,875 B1* | 3/2019 | Kopelman | ............ G06T 1/0007 |
| 2007/0203599 A1 | 8/2007 | Shibata et al. | |
| 2008/0261165 A1 | 10/2008 | Steingart et al. | |
| 2012/0095732 A1 | 4/2012 | Fisker et al. | |
| 2018/0005371 A1* | 1/2018 | Sabina | ...................... G06T 7/11 |
| 2018/0228578 A1* | 8/2018 | Liston | .................... A61C 8/008 |
| 2020/0281699 A1* | 9/2020 | Patrioli | .................. A61C 9/004 |
| 2020/0306010 A1* | 10/2020 | Aamodt | ................. A61C 19/06 |

* cited by examiner

*Primary Examiner* — Todd Buttram
(74) *Attorney, Agent, or Firm* — Knobbe, Martens, Olson & Bear, LLP

(57) ABSTRACT

Systems and methods for enhanced techniques for determination of dental margins in intraoral scans. An example method includes receiving a request including an intraoral scan of a portion of a mouth, the intraoral scan depicting a margin created via adjustment of a tooth. A prepared region depicting the tooth is identified based on the intraoral scan. A representation of the intraoral scan usable as input to a machine learning model is generated, with the representation comprising structured data associated with the point cloud or mesh. Information identifying an estimated margin is determined based on the representation via computing a forward pass of the machine learning model. A response comprising the determined information is generated, with the determined information being usable to fabricate a prosthetic according to the estimated margin.

20 Claims, 14 Drawing Sheets

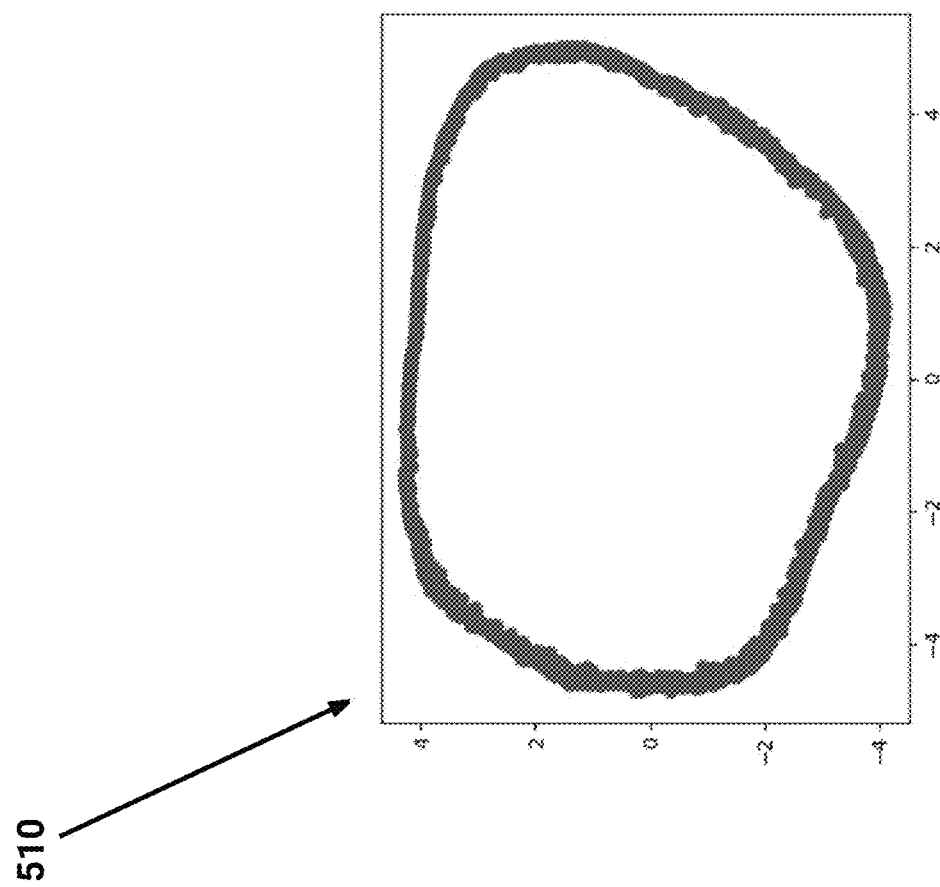

ENHANCED TECHNIQUES FOR DETERMINATION OF DENTAL MARGINS IN INTRAORAL SCANS

BACKGROUND

Field

The present disclosure relates to computer vision techniques and, more particularly, enhanced techniques for determining a dental margin.

Description of the Related Art

In dentistry, it is common for patients to receive prosthetics to address dental issues of a cosmetic and/or medical nature. Example prosthetics may include crowns, bridges, implants, veneers, and so on. Since a prosthetic is attached into a patient's mouth, it is paramount that the positioning of the prosthetic be correct. With respect to a crown, a dentist may prepare a patient's tooth to receive a crown. As an example, the dentist may adjust an edge of the patient's tooth such as by cutting the tooth. A crown may then be created to meet this adjusted edge. In this way, the crown may be customized to provide for a comfortable, and well fitting, prosthetic. The edge, as an example, may be referred to as a margin. Thus, the efficacy of a fabricated crown may be based partly on techniques to accurately identify the margin from an impression of the tooth. As is known in the art, an improperly determined margin may lead to medical issues with respect to the crown. For example, an 'open margin' may result when a gap appears between a crown and an edge of a patient's tooth.

Current techniques to identify a margin are time intensive. For example, impressions may be taken by a dentist. These impressions may then be provided to an outside entity for use in creation of a prosthetic. Additionally, digital impressions may be obtained using intraoral scanners. However, intraoral scans may be of varying quality. As an example, a margin may not be clearly identifiable from an intraoral scan owing to preparation of a patient's mouth or problems with operating the intraoral scanner. This may lead to such software-based techniques being unreliable and resulting prosthetics being ill-fitting.

BRIEF DESCRIPTION OF THE DRAWINGS

The foregoing aspects and many of the attendant advantages will become more readily appreciated as the same become better understood by reference to the following detailed description, when taken in conjunction with the accompanying drawings, wherein:

FIG. 5B illustrates example two-dimensional output associated with one or more machine learning models.

DETAILED DESCRIPTION

Figure 1A:
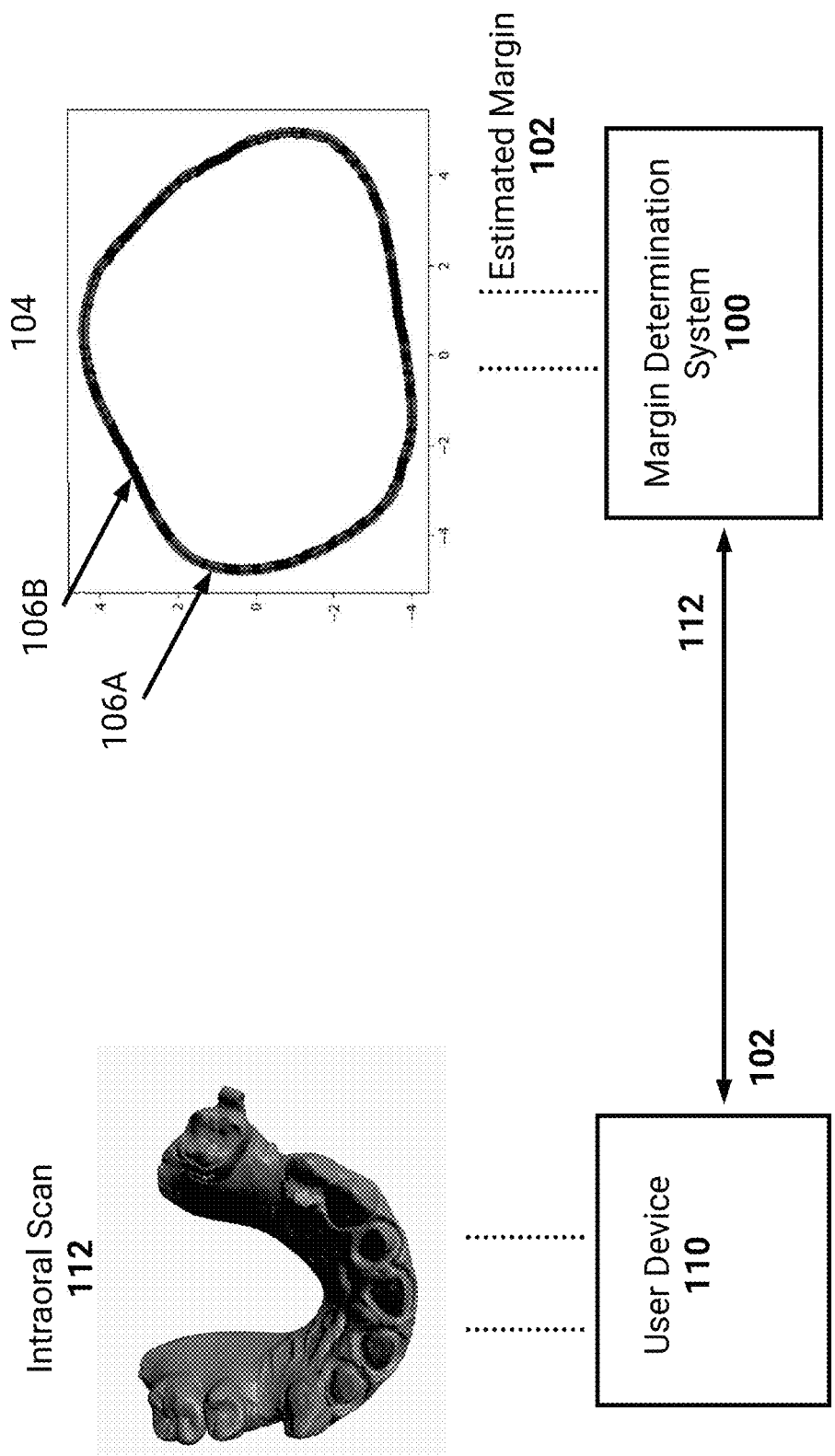
FIG. 1A illustrates a block diagram of an example margin determination system in communication with a user device.

Generally described, aspects of the present disclosure relate to automated techniques for estimating a margin or finishing line based on one or more intraoral scans of a portion of a patient's mouth. As described herein, a margin may represent a location at which a portion of a patient's mouth is to be in contact with, or otherwise receive, a prosthetic. In some instances, a margin line may alternatively be referred to as a finishing line or preparation line. An example portion of a patient's mouth may include one or more teeth or a portion thereof. Example prosthetics may include crowns, bridges, implants, veneers, and so on. As will be described in more detail, a system as described herein may use example machine learning techniques to estimate a margin for use in fabricating a prosthetic. Due to the enhanced techniques described herein, the resulting prosthetic may be more rapidly fabricated while also more accurately adhering to a margin.

INTRODUCTION

A prosthetic, such as a crown, may be designed to fit precisely into a patient's mouth. For example, the patient may have a tooth which requires dental restoration. In this example, a dental professional may prepare the tooth for placement of the crown. As an example, the dental professional may cut the tooth using a rotary dental headpiece and/or a laser to make space for the crown. This cut portion of the tooth may be removed due to dental decay and/or for structural reasons. The crown may then be designed for placement at the tooth, such that it provides a lasting correction in the patient's mouth. As may be appreciated, the above-described dental professional may obtain an impression of, at least, the prepared tooth. This impression may then be used to inform the fabrication of the crown. To increase a speed at which an impression may be taken, digital impressions are increasingly being utilized.

Example impressions may be based on intraoral scans of the patient's mouth. For example, an intraoral scanner may be used which allows for the capture of direct optical impressions. In this specification, an intraoral scan may include information indicative of geometrical information associated with the patient's mouth. An example intraoral scan may include a point cloud. For this example intraoral scan, the point cloud may include a multitude of points representing three-dimensional locations corresponding to an inside of the patient's mouth. The point cloud may be sufficiently dense to enable an accurate representation of the patient's mouth. Another example intraoral scan may include a mesh. For this example intraoral scan, the mesh may be a three-dimensional surface model of the patient's mouth. As an example, the three-dimensional surface model may include a multitude of polygonal shapes.

With respect to the example of a crown above, the dental professional may analyze an intraoral scan to identify a margin depicted in the intraoral scan. A margin may indicate positioning associated with a prepared tooth which the crown is to match. For example, the margin may be used to mark a transition between the crown and the prepared tooth. There may be a multitude of different types of margins. Example types may include a knife edge, chamfer, deep chamfer, radial shoulder, radial shoulder with a bevel, classic shoulder, and so on.

At present, these different types of margins may cause inaccuracies with respect to fabrication of a prosthetic based on such intraoral scans. For example, deeper margin lines may be difficult to identify from an intraoral scan. In this example, an intraoral scanner may be unable to scan certain portions of a patient's mouth (e.g., a portion may be behind a gum). Therefore, a resulting prosthetic may fit poorly into a patient's mouth. This may result in adjustments needing to be made to the prosthetic or to the patient later experiencing issues. Therefore, while intraoral scans may reduce a time until an impression may be obtained, they may also introduce ambiguities when the intraoral scans are later analyzed by a dental professional.

As will be described in more detail below, a system described herein (e.g., the margin determination system 100) may use machine learning techniques to accurately estimate a margin based on one or more intraoral scans. An example machine learning technique may include use of a convolutional neural network (CNN). For this example technique, the CNN may include a multitude of convolutional layers, pooling layers, dense layers (e.g., fully connected layers), and so on. The convolutional layers may include volumes of filters which may be trained by the system to identify features indicative of a margin. In some embodiments, one or more dense layers may be used to assign confidence values, or probabilities, associated with an estimated margin.

Advantageously, the machine learning techniques may address the above-described deficiencies of analyzing intraoral scans. For example, the system may rapidly extract a margin from an intraoral scan regardless of the type of margin depicted in the scan. In this way, the system may allow for a more accurately fabricated prosthetic as compared to prior techniques. Additionally, the system may provide an added degree of repeatable success as compared to prior techniques. As an example, a margin may be estimated with a greater routine accuracy.

As described herein, the estimated margin may include information indicative of a margin associated with one or more intraoral scans. For example, the system may identify points, or locations, within an intraoral scan which form an estimated margin. As another example, the system may assign a label to a portion of the intraoral scan which forms the estimated margin. In some embodiments, the system may generate a data structure which includes information identifying an estimated margin. For example, a JavaScript Object Notation (JSON) file may be created which identifies potions of an intraoral scan which form an estimated margin. In this way, a prosthetic may be fabricated based on the information included in the JSON file. Optionally, the system may package an estimated margin in a format, schema, and so on, associated with software used to fabricate a prosthetic. As an example, the package may conform to a particular three-dimensional printing format.

Figure 7A:
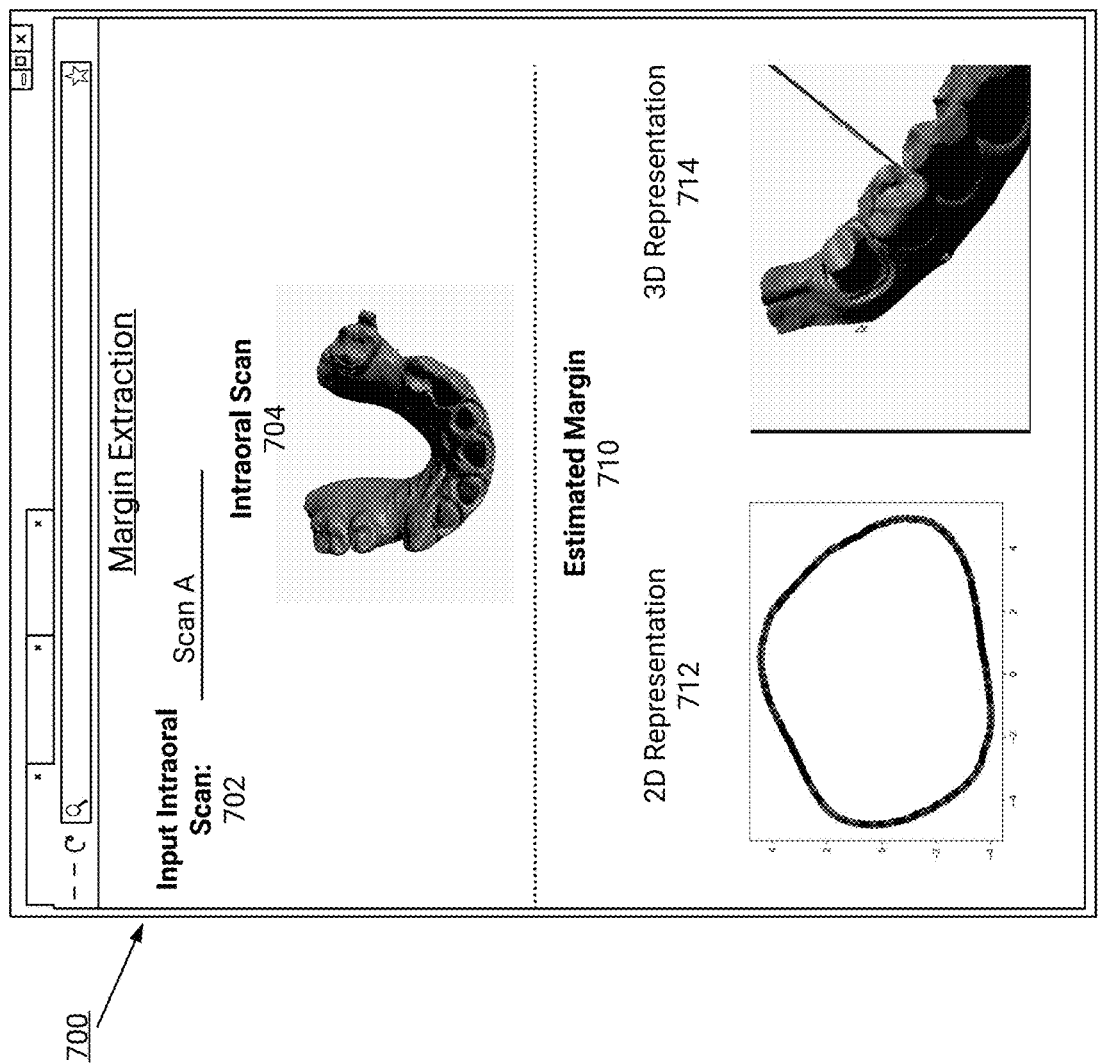
FIGS. 7A-7B illustrate an example user interface presenting an example estimated margin.
Figure 7B:
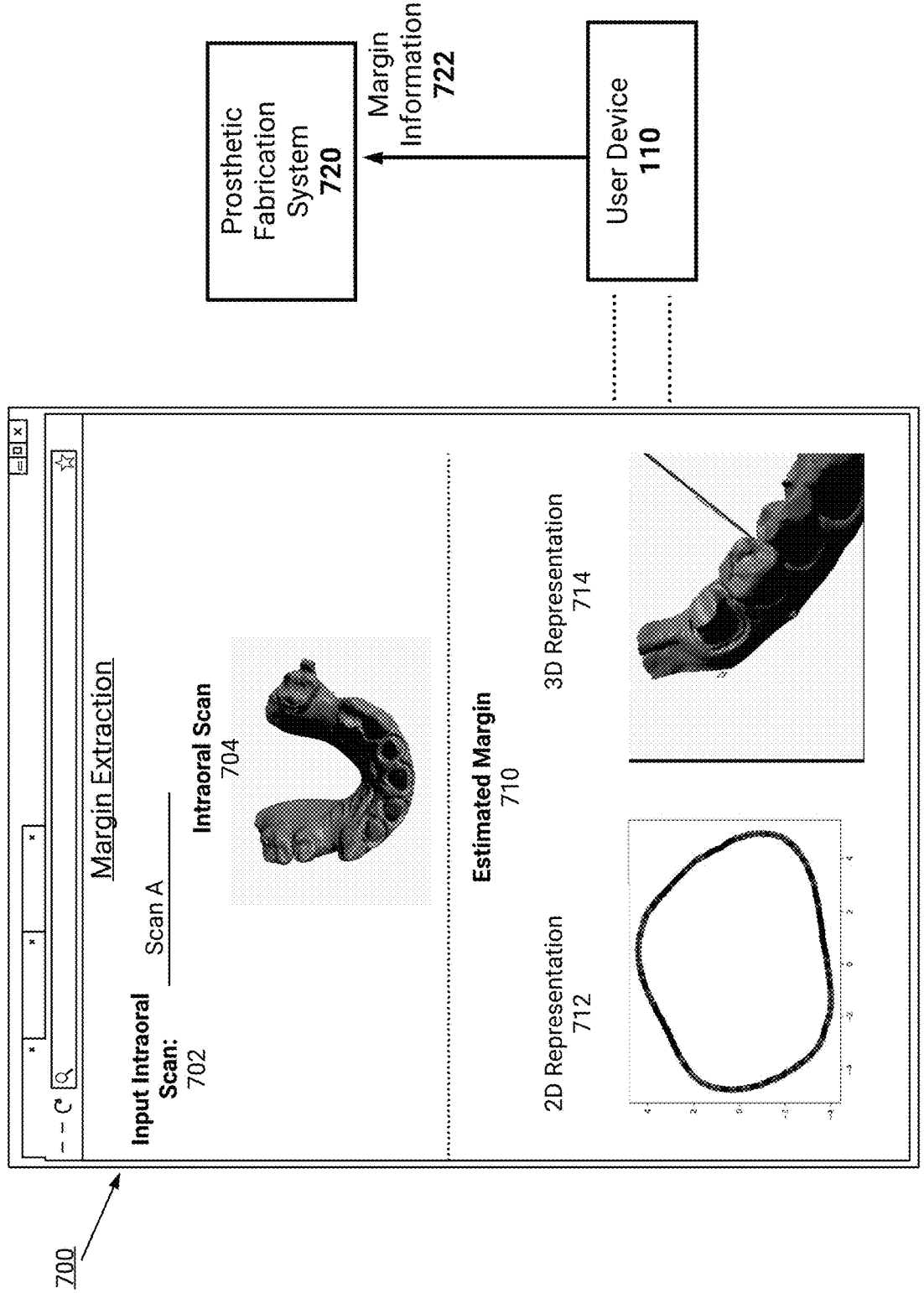

The system described herein may respond to application programming interface (API) calls from user devices in communication with the system. As an example, an API platform may be leveraged by user devices via which intraoral scans may be provided. In some embodiments, the user devices may use a user interface described herein to provide intraoral scans. An example user interface is illustrated in FIGS. 7A-7B and described in more detail below. In response, the system may generate estimated margins based on the intraoral scans. These estimated margins may then be similarly provided as a response via the API platform. In one embodiment, the API response or data structure generated by the system in a given instance may include, for each of potentially multiple margins identified in a given intraoral scan: (a) indication of the number of points making up the margin, (b) confidence values on a per-point basis and/or confidence of the margin as a whole, and (c) the point coordinates making up the polyline(s) or sub-point cloud(s) of the margin. The output may additionally include an indication of scan quality, separate from the margin quality or margin confidence information.

In some embodiments the system may be associated with a web application. In this example, user devices may access the web application via a web browser. The functions described herein, such as providing intraoral scans and/or receiving estimated margins, may be associated with endpoints. For example, a network endpoint may be publicly accessible by user devices. In this example, a user device may therefore provide a request identifying an intraoral scan via the network endpoint. The system may analyze the intraoral scan and generate an estimated margin. As described above, the system may provide the estimated margin as a data structure (e.g., a JSON or XML file) in response to the request.

In this way, the system described herein may receive requests and generate responses to a multitude of user devices. Optionally, the system may generate quality score information associated with a request. The quality score information may be used by a requesting user device to inform fabrication of a prosthetic. For example, the quality score information may indicate that an estimated margin has a low confidence of accuracy. In this example, the requesting user device may provide a new intraoral scan for analysis by the system. Due to the enhanced machine learning techniques described herein, the system may rapidly estimate a margin from the new intraoral scan. In this way, a margin may be identified in real-time (e.g., substantially real-time) while a patient is in a dental office.

As will be described, quality score information may reflect one or more quality measures associated with an intraoral scan provided in the request. For example, a quality measure may reflect a denseness of a point cloud represented by an intraoral scan. Quality score information may further reflect one or more quality measures associated with an estimated margin. For example, the system may determine a variance of curvature along a line forming the estimated margin. In this example, an increased variance may be associated with a reduced quality score. Additional description relating to quality score information is included below.

The techniques described herein therefore address technological problems and improve prior techniques to identify margins. As described above, intraoral scans may be ambiguous as to a location of a margin. In this way, a dental professional may improperly identify the margin based on an intraoral scan. In contrast, the system described herein leverages machine learning techniques to accurately identify a margin. Optionally, the system may correct for an intraoral scan which includes errors. As an example, a portion of a patient's tooth may be incorrectly depicted in an intraoral scan due to errors associated with the use or functioning of an intraoral scanner. In some embodiments, and as will be described, the system may use a generative model to generate an estimated margin for the portion. Thus, the techniques described herein may reduce a time associated with fabrication of a prosthetic. Additionally, the resulting prosthetic may more closely to adhere to a margin of a tooth prepared by a dental professional.

Example Block Diagrams

FIG. 1A illustrates a block diagram of an example margin determination system 100 in communication with a user device 110. As illustrated, the margin determination system 100 may receive an intraoral scan 112 from the user device 110 and generate an estimated margin 102 based on the scan 112. In some embodiments, the margin determination system 100 may be a system of one or more computers, one or more virtual machines executing on a system of one or more computers, and so on. The user device 110 may, for example, be a laptop, tablet, wearable device, mobile device, augmented and/or virtual reality device, and so on. In some embodiments, the user device 110 may execute software which performs the functionality described herein. For example, the user device 110 may obtain an intraoral scan 112 and generate a corresponding estimated margin 102. In this example, the user device 110 may optionally obtain an application (e.g., an 'app') which effectuates the generation of the estimated margin 102.

The user device 110 may optionally provide information to the margin determination system 100 via a network (e.g., the internet). For example, the user device 100 may communicate information via a secure connection (e.g., an HTTPS connection) established with the margin determination system 100. Optionally, in some embodiments the system 100 may respond to application program interface (API) calls or endpoints. Thus, the user device 110 may provide the intraoral scan 112 via an API call or endpoint.

The intraoral scan 112, as described above, may represent a scan of a patient's mouth captured by an intraoral scanner. As an example, the intraoral scanner may be moved about the patient's mouth. During movement of the patient's mouth, the intraoral scanner may output light (e.g., coherent light, structured light, and so on). A portion of the output light may be received by the intraoral scanner and used to determine geometrical information associated with the patient's mouth. For example, a point cloud may be generated. In this example, the point cloud may indicate three-dimensional locations of points on respective surfaces of the patient's mouth. The margin determination system 100 may therefore obtain the intraoral scan 112 as a point cloud. The information may include, for example, three-dimensional locations associated with each point in the point cloud.

In some embodiments, the intraoral scan 112 may be a mesh. For example, an intraoral scanner, or software in communication with the intraoral scanner, may generate a three-dimensional mesh. The mesh may include a multitude of polygons, or other surface representations, which indicate geometrical information associated with the patient's mouth. For example, the mesh may represent information as a set of faces and a set of vertices (e.g., face-vertex meshes). In some embodiments, the margin determination system 100 may generate a mesh based on a point cloud obtained from an intraoral scanner. As an example, certain known techniques may be leveraged by the margin determination system 100 (e.g., MeshLab).

As will be described, the margin determination system 100 may analyze the intraoral scan 112 via one or more machine learning models. Example machine learning models may include dep learning models, such as neural networks, convolutional neural networks (CNN), and/or recurrent neural networks (RNN). With respect to a CNN, the intraoral scan may be analyzed via volumes of filters. Advantageously, these filters may leverage the volumetric information indicated by the intraoral scan 112. Certain example machine learning models may use occupancy grids. For example, certain points within a point cloud may be assigned to respective bounding boxes. In this example, a portion may be defined as an intersection of the point cloud with a bounding box.

As will be described below, one or more of the above-described machine learning models may be used to generate the estimated margin 102. In some embodiments, a machine learning model may determine a confidence associated with each point in a point cloud forming the estimated margin 102. Points having respective confidences exceeding a threshold may be assigned as forming the estimated margin 102.

Optionally, the margin determination system 100 may use both a point cloud and a mesh associated with an intraoral scan 112. For example, the margin determination system 100 may receive a point cloud from a first usage of an intraoral scanner and a mesh from a second usage of an intraoral scanner. As another example, the margin determination system 100 may generate the mesh from a received point cloud. The margin determination system 100 may use a first machine learning model which is trained using point clouds to determine the estimated margin 102. In this example, the margin determination system 100 may assign points within the point cloud as forming the estimated margin 102. As another example, the margin determination system 100 may use a second machine learning model which is trained using meshes. In this example, the margin determination system 100 may assign certain triangles, polygons, and so on, as forming the estimated margin 102. The margin determination system 100 may then analyze the outputs of these respective models. The outputs may be used to refine the estimated margin 102. For example, certain points assigned as forming the margin may be removed, or adjusted, if they do not fall within triangles or polygons which are assigned as forming part of the margin.

As will be described below in more detail, the estimated margin 102 may be refined. It may be appreciated that certain points may be inaccurately assigned (e.g., labeled) by a machine learning model as forming the estimated margin 102. As an example, certain points may be further than a threshold distance from other points forming the estimated margin 102. Thus, these points may be discarded. To refine the estimated margin 102, the margin determination system 100 may use interpolation techniques. For example, the margin determination system 100 may determine measures of central tendency associated with the margin line 102. This information may include an average rate of curvature, rates of curvature in localized portions of the margin line 102, angular distances between points in localized portions, and so on. Certain points may be refined which deviate from these measures of central tendency. Thus, the resulting margin 102 may represent a line which a dental professional is likely to have made by preparing a patient's tooth.

The refined points may additionally be used as training information to refine parameters of a machine learning model. For example, the machine learning model may incorrectly characterize certain points as forming a margin line. In some embodiments, the margin determination system 100 may determine a loss associated with these incorrectly characterized points via a loss function. Based on backpropagation techniques (e.g., stochastic gradient descent), the parameters of the machine learning model may be updated. In some embodiments, a user of the margin determination system 100 may confirm the incorrect characterization of the points prior to updating of the model.

Information describing the estimated margin 102 may then be provided to the user device 110. As an example, the information may include points included in the intraoral scan 112 which form the estimated margin 102. As another example, the information may include triangles or polygons included in the intraoral scan 112 which form the estimated margin 102. The margin determination system 100 may then provide the information to the user device 110, such as in a JavaScript Object Notation (JSON) format. In some embodiments, the margin determination system 100 may determine a confidence associated with the estimated margin 102. For example, the system 100 may determine a confidence associated with each point or polygon assigned as forming the estimated margin.

The margin determination system 100 may generate graphical representations of the estimated margin 102. As will be described below, with respect to FIGS. 7A-7B, these graphical representations may be included in a user interface presented via the user device 110. In this way, a user of the user device 110 may rapidly view the resulting estimated margin 102 in a succinct format. In the illustrated example, a graphical representation 104 may be a two-dimensional representation of the margin line. This representation 104 may be useful to quickly view a shape associated with the margin line. Optionally, the graphical representation 104 may include information indicative of a confidence associated with each point forming the line. For example, point 106B may indicate a high confidence while point 106A may indicate a lower confidence.

While intraoral scanners are described herein, it may be appreciated that additional devices and systems may be employed and fall within the scope of the disclosure. For example, in some embodiments stereo cameras may be used to obtain images of a patient's mouth. In this example, stereoscopic techniques may be used match points within pairs of stereo images. Based on these matches, depth information may be determined. Thus, a three-dimensional representation of an interior portion of the mouth may be determined.

Figure 1B:
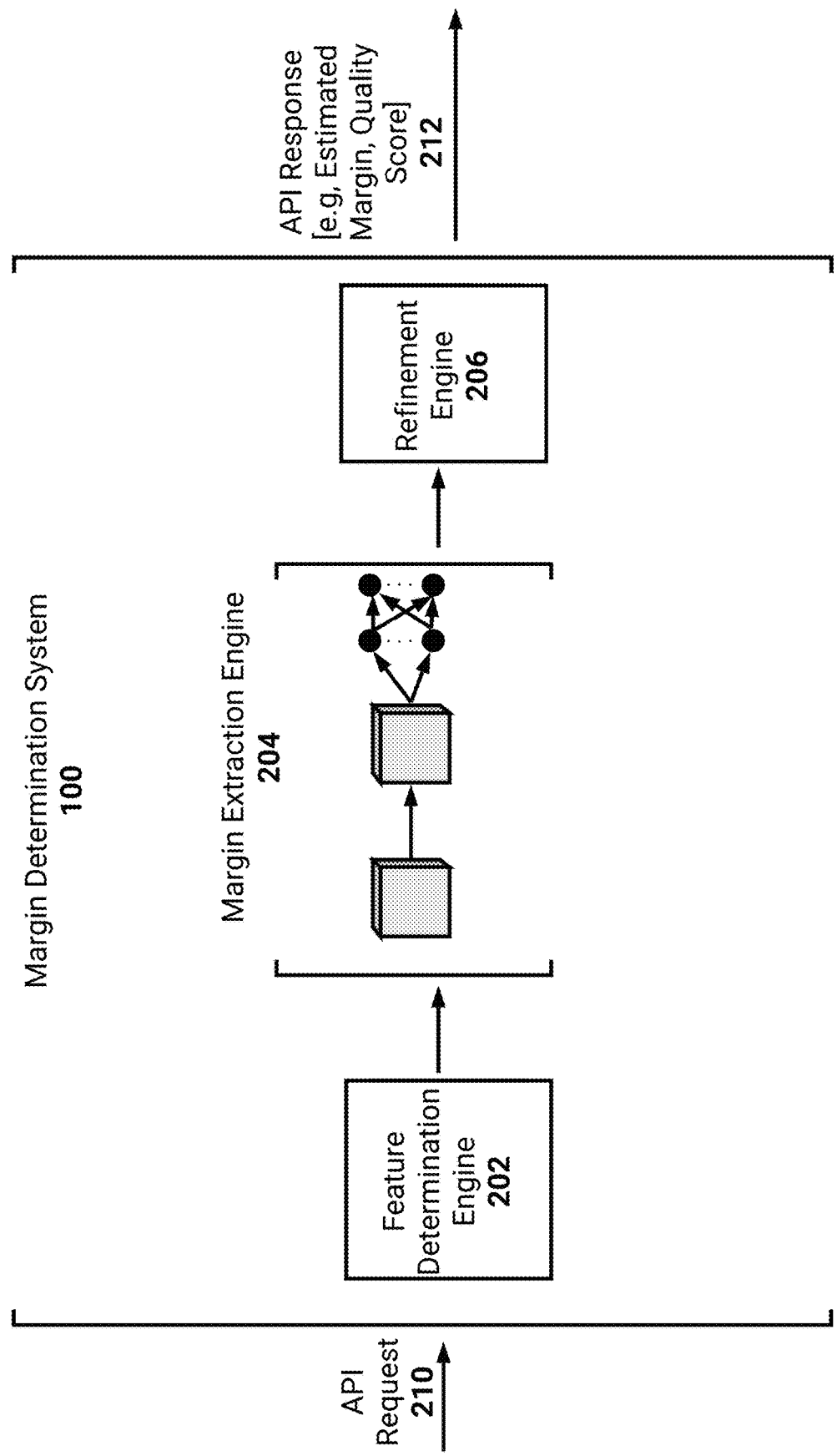
FIG. 1B illustrates a block diagram of the example margin determination system generating an estimated margin.

FIG. 1B illustrates a block diagram of the example margin determination system 100 generating an estimated margin 102. In the illustrated example, margin determination system 100 responds to an API request 210. As described above, the system 100 may respond to API calls or endpoints. For example, an API gateway may be used as a point of entry to the margin determination system 100. Thus, a user device may provide information to the system 100 for processing (e.g., via a network). In the illustrated example, the API request 210 may include one or more intraoral scans of a portion of a patient's mouth.

The margin determination system 100 may analyze a received intraoral scan to identify one or more prepared regions in the scan. As described above, a dental professional may prepare a tooth for attachment with a prosthetic. For example, the dental professional may remove portions of the tooth. The intraoral scan may therefore depict the prepared tooth, such as via a point cloud or mesh. The system 100 may identify a portion of the intraoral scan as corresponding to a prepared region, for example using machine learning techniques. An example machine learning technique may include a deep learning model (e.g., a CNN), which is trained to identify prepared regions. As an example, the deep learning model may be trained using intraoral scans which include labels (e.g., bounding boxes) surrounding portions depicted prepared regions. Optionally, certain intraoral scanners may produce denser point cloud for prepared regions. Thus, the system 100 may identify prepared regions based on a density associated with regions of the point cloud.

Sub-point clouds, or sub-meshes, corresponding to the prepared regions may then be generated by the margin determination system 100. For example, points included in an identified region may be extracted. In this example, the points may represent geometrical information associated with the identified region. As another example, and with respect to the intraoral scan representing a mesh, a sub-mesh may be generated which corresponds to a particular prepared region of the mesh. Advantageously, the margin determination system 100 may analyze these sub-point clouds or sub-meshes. In this way, the system 100 may reduce required processing resources and computation time.

The margin determination system 100 includes a feature determination engine 202 to extract features associated with each prepared region. As will be described, these features may be used by a machine learning model. An example feature may include mean curvature information for a prepared region. This example feature may indicate curvature associated with a surface of the prepared region. Another example feature may include Gaussian curvature information. For example, the feature determination engine 202 may determine the Gaussian curvature for points included in a point-cloud depicting the prepared region. For a sub-mesh depicting the prepared region, the engine 202 may determine the Gaussian curvature for one or more points normal to each polygon or triangle included in the sub-mesh. Another example feature may include geodesic curvature for surfaces and/or points associated with the prepared region.

The margin determination system 100 further includes a margin extraction engine 204, which may execute one or more machine learning models. For example, the margin extraction engine 204 may compute a forward pass of a machine learning model. In this example, an input to the machine learning model may represent a point cloud or mesh associated with a prepared region. The input may also represent features extracted by the feature determination engine 202 for the prepared region.

The margin extraction engine 204 may optionally map the input into disparate forms, such as different structured data forms, based on a machine learning model used by the engine 204. For example, the margin extraction engine 204 may generate a voxel grid via voxelization techniques. In this example, voxels may be created which include a subset of points, or polygons, included in a point cloud or mesh. As described above, an example technique may include intersecting bounding boxes with a point cloud or mesh of a prepared region. In some embodiments, occupancy grids and/or distance fields may be used. In some embodiments, the engine 204 may stack three-dimensional locations associated with points included in a voxel. These stacked locations may be used as input features to a machine learning model.

To determine an estimated margin, the margin extraction engine 204 may then determine an output associated with one or more machine learning models. With respect to the voxelization techniques described above, the margin extraction engine 204 may compute a forward pass through PointGrid, ShapeNet, VoxNet, and so on. Additional machine learning models may be used and fall within the scope of the disclosure herein. An example machine learning model used by the margin extraction engine 204 may generate an indication of a location of an estimated margin on a prepared region identified by the margin determination system 100. For example, and with respect to a received intraoral scan being a point cloud, the margin extraction engine 204 may identify points in the point cloud which form the estimated margin. In this example, the points may be included in voxels which were identified as being part of the estimated margin with greater than a threshold likelihood. With respect to the intraoral scan being a mesh, the margin extraction engine 204 may identify portions of the mesh (e.g., triangles, polygons, surfaces) which are identified as being part of the estimated margin with greater than a threshold likelihood.

In some embodiments, portions of a point cloud may not include points for an entirety of a prepared region. For example, an intraoral scanner may have failed to obtain information for a portion of the prepared region (e.g., the portion may be behind a gum of a tooth or the scanner may have been improperly used). As another example, the intraoral scanner may have points for a portion with less than a threshold density. In some embodiments, the margin extraction engine 204 may use generative modeling techniques to generate points which are likely to correspond to a portion of the prepared region that was obscured in the scan or for which insufficient scan data was captured. For example, a generative adversarial network (GAN) may be used to make corrections or additions to portions of a scan. In this way, corrections to an intraoral scan may be made by the system 100.

While the above described the margin extraction engine 204 computing a forward pass, it may be appreciated that in some embodiments the margin extraction engine 204 may train one or more of the machine learning models. As an example, the margin extraction engine 204 may receive a multitude of point clouds depicting prepared regions. These point clouds may optionally be separated into a training and validation set. Within the training set of point clouds, certain points may be identified as forming a known margin. Similar to the above, the margin extraction engine 204 may use voxelization techniques to generate voxels which include a portion of the points. The margin extraction engine 204 may then compute a forward pass through a particular machine learning model. For example, the particular machine learning model may be defined according to certain hyperparameters (e.g., a number of layers, types of layers, numbers of filters, activation functions, dropout rate, and so on) and parameters (e.g., filter values, weight values, and so on). One or more losses may be determined based on the forward pass, and the engine 204 may update the parameters of the particular machine learning model.

The above-described training process may then be repeated at least a threshold number of times on the training set. In some embodiments, models of varying hyperparameters may be trained. A particular machine learning model may be selected based on accuracy with respect to the validation set described above.

As may be appreciated, deep learning models may benefit from large training sets. In some embodiments, the training sets used to train the machine learning models described herein may be sufficient to generate accurate estimations of margins. In some embodiments, the margin extraction engine 204 may use transfer learning techniques to enhance potentially limited training data sets. For example, it may be difficult to obtain more than a threshold number (e.g., thousands, tens of thousands) of points cloud which depict prepared regions with known margins. In this example, the margin extraction engine 204 may obtain a deep learning model which has been previously trained. For example, the machine learning models described herein may be trained to understand geometry associated with shapes depicted in point clouds or meshes. Thus, the margin extraction engine 204 may obtain pre-trained versions of these machine learning models. An example of such a machine learning model is ShapeNet. The engine 204 may then use transfer learning techniques to update the pre-trained machine learning models using intraoral scans.

For example, a particular machine learning model may be used to classify an object represented by a point cloud or mesh. In this example, the particular machine learning model may include a multitude of convolutional layers. In some embodiments, the margin extraction engine 204 may obtain trained values of parameters for this particular machine learning model. Without being constrained by theory, earlier convolutional layers may be understood to learn lower level features while later convolutional layers may be understood to learn higher level features. For example, the higher level features may correspond with features indicative of classes of objects. The margin extraction engine 204 may therefore train parameters of the particular machine learning model starting from a certain convolutional layer within the model. Parameters from earlier convolutional layers may be fixed. In this way, the engine 204 may allow for features indicative of a prepared region, margin, and so on, to be learned by these later convolutional layers.

Similarly, the margin extraction engine 204 may adjust a number of layers associated with a machine learning model. As an example, the engine 204 may supplement the layers with one or more fully-connected layers. These additional layers may enable assignment of points or portions of a mesh which form an estimated margin. Additionally, these additional layers may enable assignment of a confidence or probability associated with the estimated margin. The engine 204 may also adjust hyperparameters of an existing layer.

As an example, the engine 204 may allow for additional categories or classes to be added to an existing machine learning model. In this example, the additional categories or classes may relate to prepared regions, margins, and so on.

In this way, the margin extraction engine 204 may determine an estimated margin for each prepared region identified from the intraoral scan included in the request 210. The margin determination system 100 may then optionally refine the estimated margins using a refinement engine 206. For example, the refinement engine 206 may determine a best sparse representation for points forming the estimated margin. As described above, certain points or portions of a mesh may be improperly assigned as forming an estimated margin. In some embodiments, the refinement engine 206 may use clustering techniques to improve the estimated margin.

As an example of a clustering technique, the refinement engine 206 may determine a centroid of the estimated margin along the length of the margin. For example, the refinement engine 206 may determine a centroid based on a cross-section of the estimated margin. The refinement engine 206 may then determine measures of central tendency associated with the estimated margin. As an example, an average distance of a cross section about a centroid may be determined. The refinement engine 206 may then remove points assigned as forming the margin which are greater than a threshold angular distance from a centroid. With respect to a cross-section, the refinement engine 206 may remove points which are farther than an average distance measure from the centroid.

Optionally, in some embodiments, the refinement engine 206 may determine discontinuities with the estimated margin. As an example, certain points assigned as forming the estimated margin may be separated from other points. Based on this separation exceeding a threshold distance measure, the points may be removed from the estimated margin. Additional refinement techniques may be used and fall within the scope of the disclosure herein. For example, the refinement engine 206 may obtain information associated with manufacturability of margins. In this example, the refinement engine 206 may optionally remove points or portions of the estimated margin which may be impractical to create for a prosthetic.

The margin determination system 100 may then obtain a final representation of the estimated margin for each of the prepared regions identified in the intraoral scan received in the request 210. An estimated margin may represent a three-dimensional surface positioned about a prepared region. An estimated margin may optionally represent a line or polyline about the prepared region. In some embodiments, the system 100 may use interpolation techniques to generate the final representation. As an example, the system 100 may use spline interpolation to smooth out the estimated margin such that a prosthetic may be readily fabricated to conform with the estimated margin.

In some embodiments, the margin determination system 100 may determine quality score information associated with the estimated margin. For example, the system 100 may determine metrics associated with the above-described technique. Based on these metrics, the system 100 may determine quality score information. Example quality score information may include a margin quality which may be normalized between 0 and 1. In some embodiments, if the margin quality is determined to be less than a threshold, the system 100 may provide a response 212 indicating that the estimated margin is not usable.

An example metric may include determining a variance of curvature along the estimated margin. Another example metric may include determining a deviance from a convex hull. As may be appreciated, a convex hull may represent a polygon or surface which encompasses a multitude of points. Thus, the system 100 may determine a convex hull based on points assigned as forming the estimated margin. A deviance from the above-described final representation of the estimated margin and the convex hull may be determined. Another example metric may include a severity of reduction during refining. For example, the system 100 may determine an extent to which points, or portions of a mesh, were removed from the estimated margin by the refinement engine 206. Another example metric may relate to a smoothness of the margin line.

Another example metric may include surface variance along, and in a neighborhood of, a portion of the received intraoral scan associated with the estimated margin. For example, the margin determination system 100 may inspect the received intraoral scan around a location of the estimated margin. The system 100 may then analyze points which were not indicated as forming the estimated margin. As an example, the system 100 may traverse the estimated margin and calculate surface properties about the margin. In this example, the system 100 may calculate surface properties for a ball centered on the estimated margin. During traversal, the system 100 may determine variance of curvature, moments of curvature, and so on. These determinations may be used to inform the above-described surface variance.

Therefore, the margin determination system 100 may determine one or more estimated margins and quality score information associated with the estimated margins. As described above, quality score information may reflect a margin quality. The requesting user device may use the margin quality to identify whether the one or more estimated margins are to be used. If the margin quality is less than a threshold, a dental professional associated with the user device may obtain one or more new intraoral scans. Optionally, the margin determination system 100 may store profile information (including one or more quality thresholds, such as a lab-specific or user-specific minimum quality score below which scans should be discarded, a quality score above which a scan should be automatically passed to an automated prosthetic fabrication process, and/or other automated responsive actions should occur) associated with dental professionals and/or labs involved in the manufacturing of a prosthetic. Thus, the system 100 may provide information to the user device indicating the margin quality is less than a stored threshold for the user device.

The estimated margins and quality score information may be provided as a response 212 to the requesting user device. As described above, the estimated margins may be provided according to a particular format (e.g., a JavaScript Object Notation representation).

Example Flowcharts/Example Margin Representations

Figure 2:
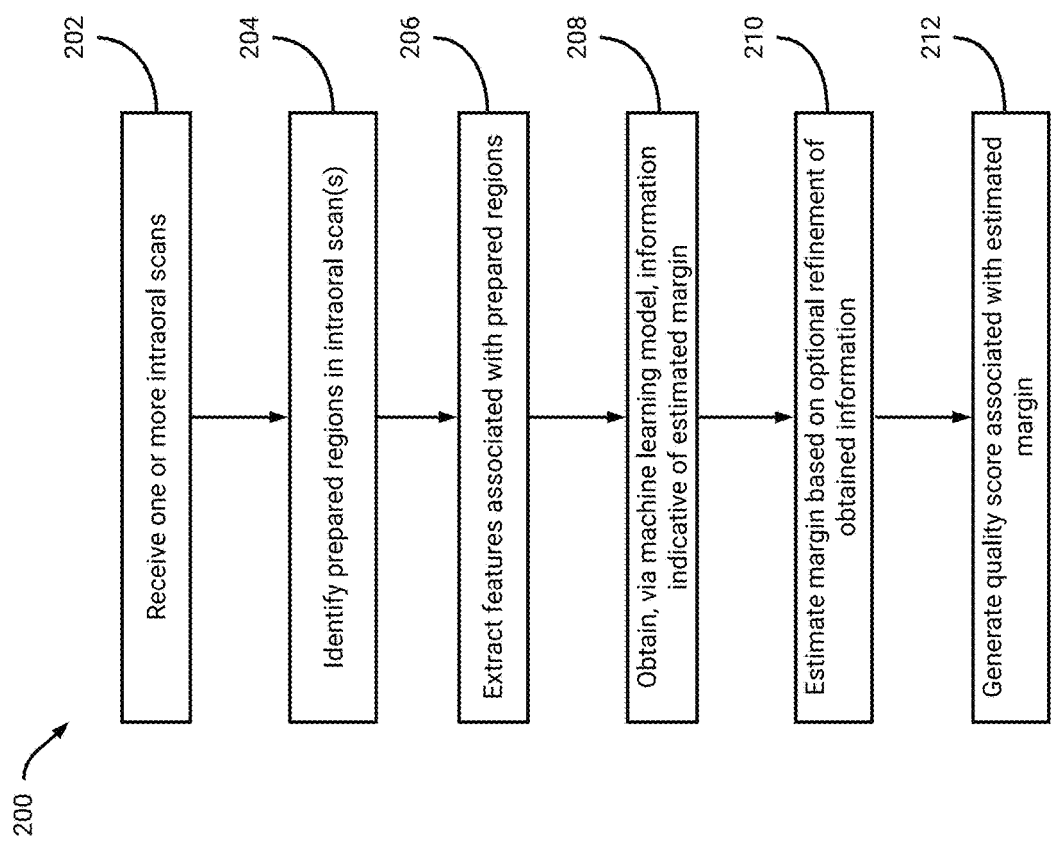
FIG. 2 illustrates a flowchart of an example process for estimating a margin according to the techniques described herein.

FIG. 2 illustrates a flowchart of an example process 200 for estimating a margin according to the techniques described herein. For convenience, the process 200 will be described as being performed by a system of one or more computers (e.g., the margin determination system 100).

At block 202, the system receives one or more intraoral scans. As described above, a user device may provide an intraoral scan via a network to the system. Optionally, the system may receive an intraoral scan directly from an intraoral scanner. For example, as a patient is at a dental office the system may obtain an intraoral scan for the patient.

Figure 3A:
FIG. 3A illustrates a graphical rendering of an example intraoral scan.

Reference will now be made to FIG. 3A. FIG. 3A illustrates an example rendering of an intraoral scan 300. The example intraoral scan 300 may be stored as a point cloud or a mesh as described above and has been rendered for display to appear as a solid surface in FIG. 3A.

In some embodiments the system may determine a scan quality associated with a received intraoral scan. For example, the system may determine whether a portion of the intraoral scan has a point cloud density less than a threshold. In this example, the system may reduce a value associated with the scan quality. If the density is less than a threshold measure, the system may provide information to the user device indicating the intraoral scan is not usable and/or should be retaken. Similarly, the system may determine whether the intraoral scan depicts one or more prepared regions (e.g., as described below). The system may also determine whether the intraoral scan includes consistent points in a point cloud. For example, the system may determine whether the intraoral scanner failed to provide consistent representations of a surface of an inside portion of a mouth. In this example, the system may determine that certain points were likely meant to be a same point. The system may also determine that certain points are erroneous and are unlikely to represent a valid inside portion of the mouth. Thus, the system may assign a value for the scan quality. IF the value is less than a threshold, the system may indicate the scan is not usable and/or should be retaken.

Returning to FIG. 2, at block 204, the system identifies one or more prepared regions in the one or more intraoral scans. The system may identify a prepared region using example machine learning techniques. In some embodiments, a density associated with a point cloud proximate to a prepared region may be greater than a density elsewhere. At block 206, the system extracts features associated with the prepared regions. As described in FIG. 1B, the features may include curvature information associated with the prepared regions.

Figure 3B:
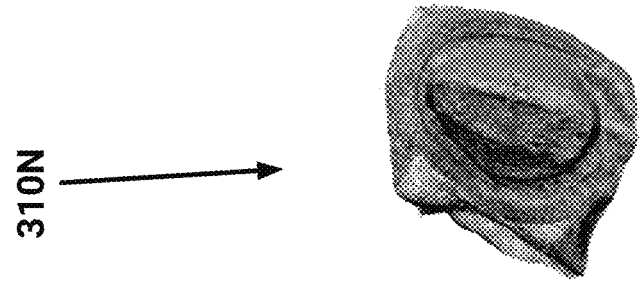
FIG. 3B illustrates example prepared regions represented in the example intraoral scan.
Figure 3B:
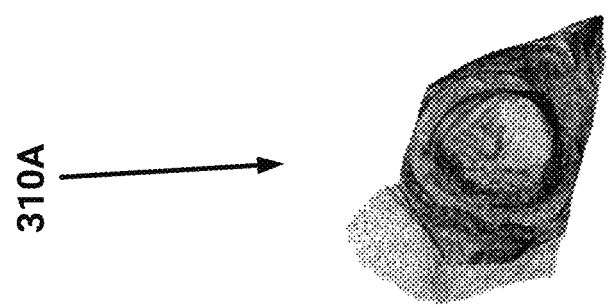

Reference will now be made to FIG. 3B. FIG. 3B illustrates example prepared regions 310A and 310N (where a number of additional regions may be identified in some instances) represented in the example intraoral scan 300 of FIG. 3A. In the illustrated example, the prepared regions 310A and 310N may represent sub-point clouds or sub-meshes generated from the intraoral scan 300. These prepared regions 310A and 310N may be provided to one or more machine learning models as described herein.

Returning to FIG. 2, at block 208, the system obtains information indicative of an estimated margin using one or more machine learning models. The features, along with a point cloud or mesh for each prepared region, may be provided as an input to a machine learning model. As discussed above, the machine learning model may have been trained to consider a combination of both the positional information (such as x, y, z coordinates) of the input mesh or point cloud data, as well as associated extracted features, in generating its output. The machine learning model may then output an indication of an estimated margin. For example, the output may indicate a confidence associated with each point in a point cloud forming an estimated margin. As another example, the output may indicate points which form the estimated margin (e.g., a label may be assigned to each point indicating whether the point forms an estimated margin).

At block 210, the system refines the estimated margin. The system may remove certain points or portions of a mesh as being associated with the estimated margin. For example, the system may remove points which are greater than a threshold distance measure from other points assigned as forming the estimated margin. The system may additionally generate a final representation of the estimated margin. For example, the system may use interpolation techniques to generate a three-dimensional surface which represents the estimated margin. The system may also generate a two-dimensional representation of a line associated with the estimated margin. The line may be used to inform an edge of a prosthetic.

At block 212, the system generates quality score information associated with the estimated margin. As described in FIG. 1B, quality score information may reflect an overall margin quality. For example, the margin quality may be normalized between zero and one. The system may determine the margin quality based on a multitude of measures. Example measures may be based on an extent to which the estimated margin was refined, curvature information, and so on as described herein.

The margin quality may optionally be used by an entity fabricating a prosthetic. For example, if the margin quality is less than a threshold the entity, or system, may indicate the estimated margin is not usable. The entity may additionally perform a review of the estimated margin in view of intraoral scans on which the estimated margin was based. In this way, the entity may optionally adjust the estimated margin.

Figure 4:
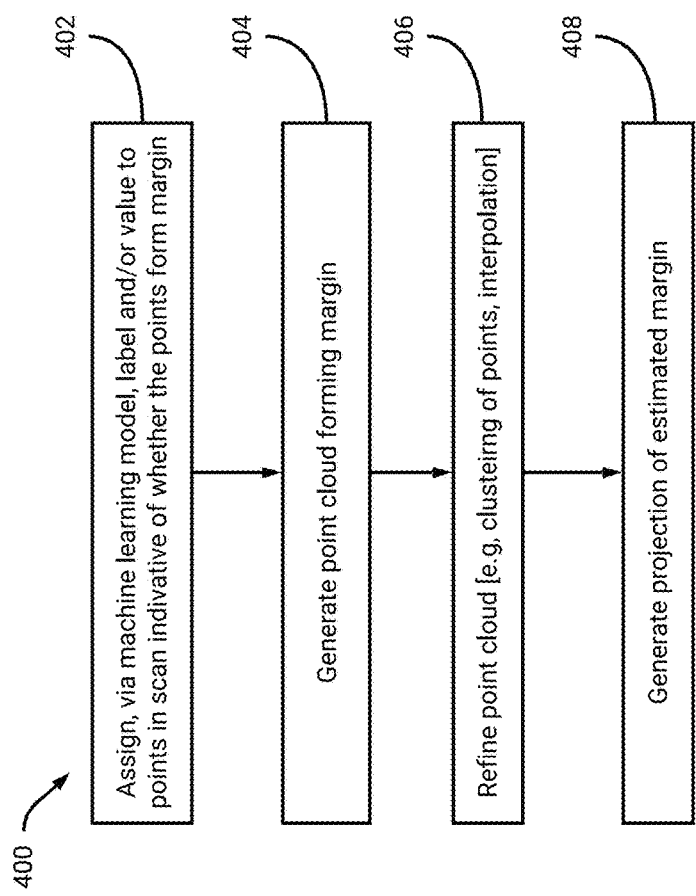
FIG. 4 illustrates a flowchart of an example process for generating an estimated margin and associated graphical representations of the estimated margin.

FIG. 4 illustrates a flowchart of an example process 400 for generating an estimated margin and associated graphical representations of the estimated margin. For convenience, the process 400 will be described as being performed by a system of one or more computers (e.g., the margin determination system 100).

At block 402, the system assigns information indicating whether points in a received intraoral scan form an estimated margin. As described above, the system may assign a value (e.g., a confidence value) to points. The system may also assign a label indicating whether a point forms part of the estimated margin, which may be determined based in part on a confidence value (e.g., whether the confidence value meets a threshold).

At block 404, the system generates a point cloud forming an estimated margin. The system may optionally generate a point cloud which includes points assigned by the system as forming the estimated margin. At block 406, the system refines the point cloud. As described in FIGS. 1B-2, the system may refine the point cloud based on clustering techniques. The system may additionally use interpolation to generate a final representation of the estimated margin.

At block 408, the system generates one or more projections associated with the estimated margin. As described above, the system may generate one or more graphical representations of an estimated margin. For example, in addition to a location of each point within a received point cloud forming the estimated margin, the system may generate graphical representations for a user to view. The graphical representations may be two or three dimensional projections associated with the estimated margin. The graphical representations may thus optionally be provided for presentation on a user device requesting the estimated margin. Example representations will be described below, with respect to FIGS. 5A-5D.

Figure 5A:
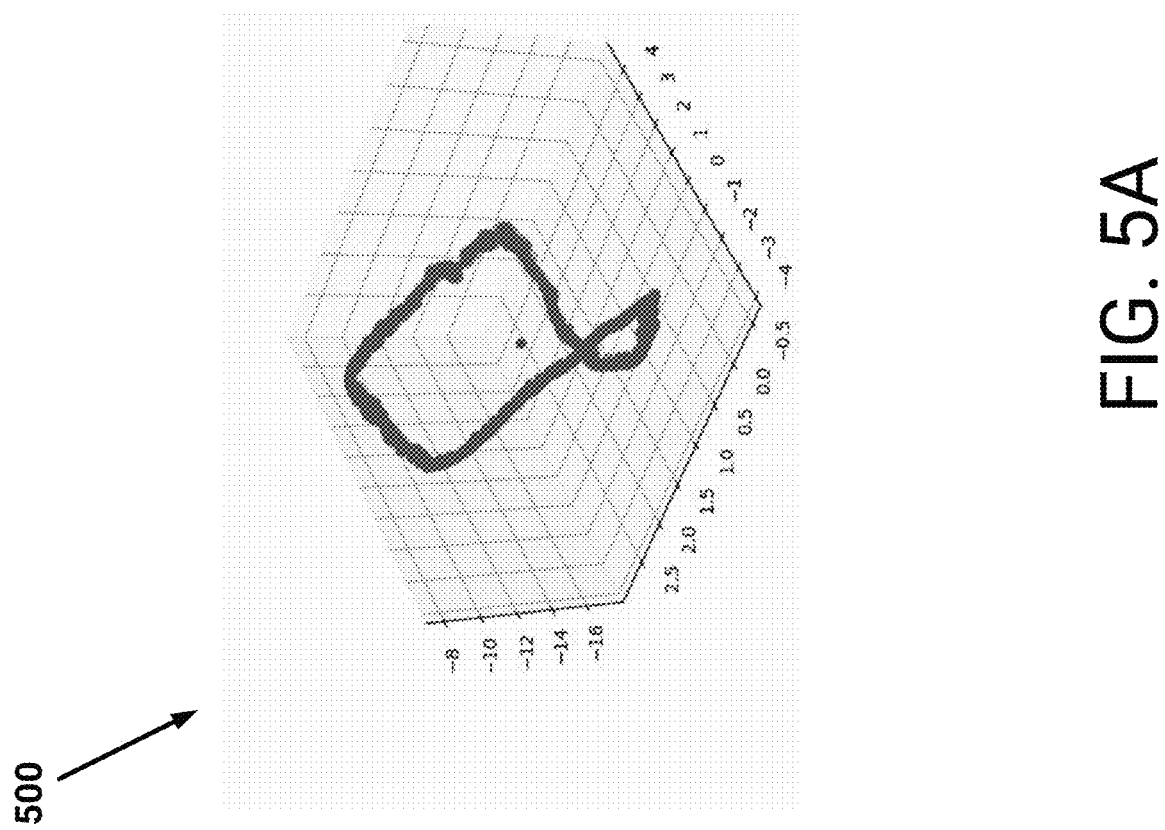
FIG. 5A illustrates example three-dimensional output associated with one or more machine learning models.

FIG. 5A illustrates example three-dimensional output 500 associated with one or more machine learning models. In the illustrated example, a three-dimensional representation of an estimated margin is included. This three-dimensional representation may reflect the estimated margin as determined by a machine learning model. For example, a user may request an output associated with the machine learning model prior to refining. As will be appreciated, FIG. 5A may be considered a graphical rendering of the output data of the machine learning model, as rendered by existing three-dimensional rendering software configured to accept a set of points or coordinates (such as x, y, z values) and render them in virtual three-dimensional space for display.

FIG. 5B illustrates example two-dimensional output 510 associated with one or more machine learning models. Similar to FIG. 5A, the two-dimensional output 510 may reflect an output associated with a machine learning model prior to refining. The output 510 may thus represent a line, such as a flattened version of the three-dimensional output 500 described above. The two-dimensional output 510 may be viewed by a user to identify whether the estimated margin corresponds with a prepared region of a patient.

Figure 5C:
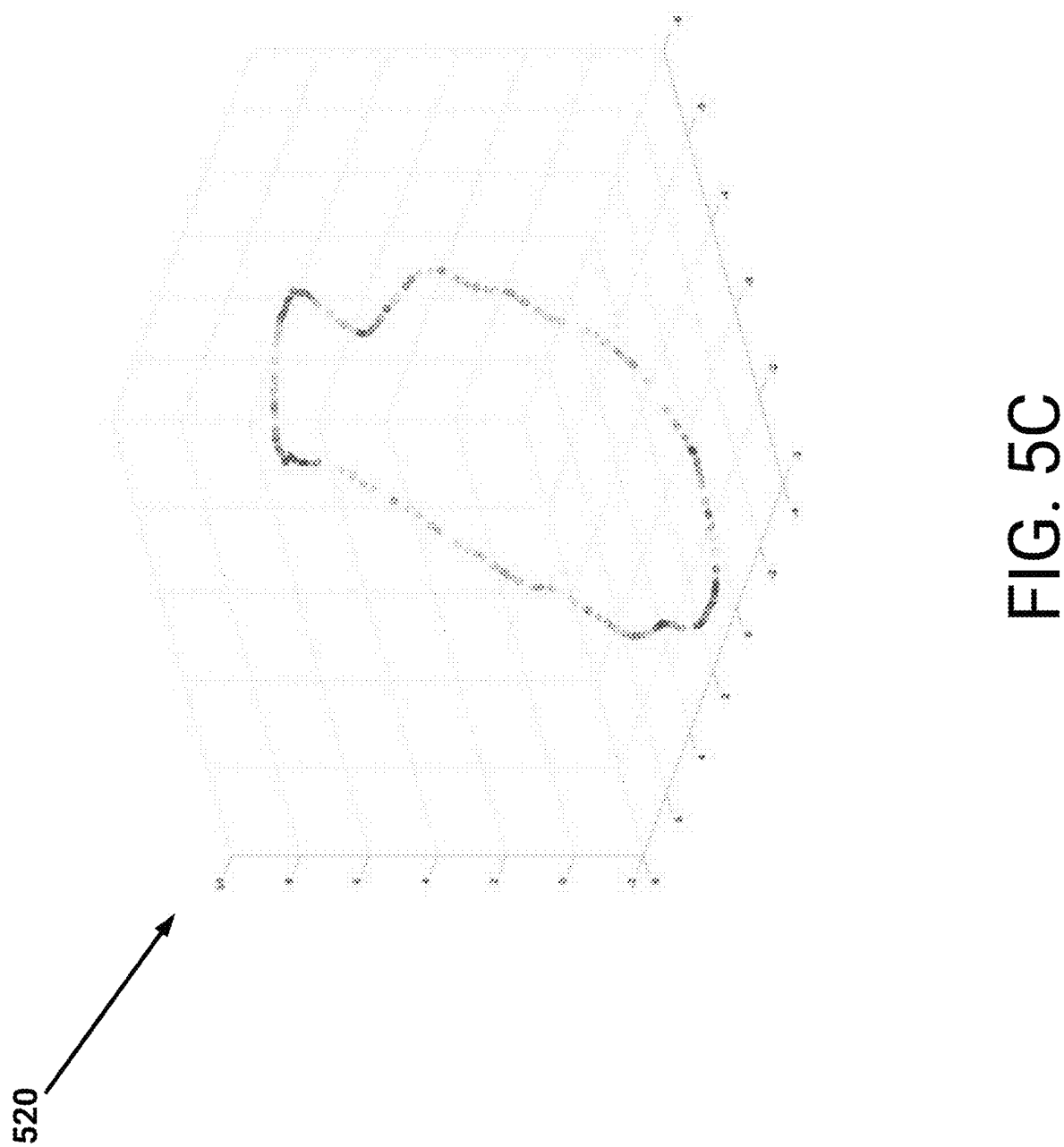
FIG. 5C illustrates example refined output associated with one or more machine learning models.

FIG. 5C illustrates a graphical rendering of an example refined output 520 associated with one or more machine learning models. In the illustrated example, the refined output 520 may represent an adjustment of the three-dimensional output 500 illustrated in FIG. 5A. Thus, this refined output 520 may be refined to remove discontinuities, to enhance a manufacturability, and so on as described herein.

Figure 5D:
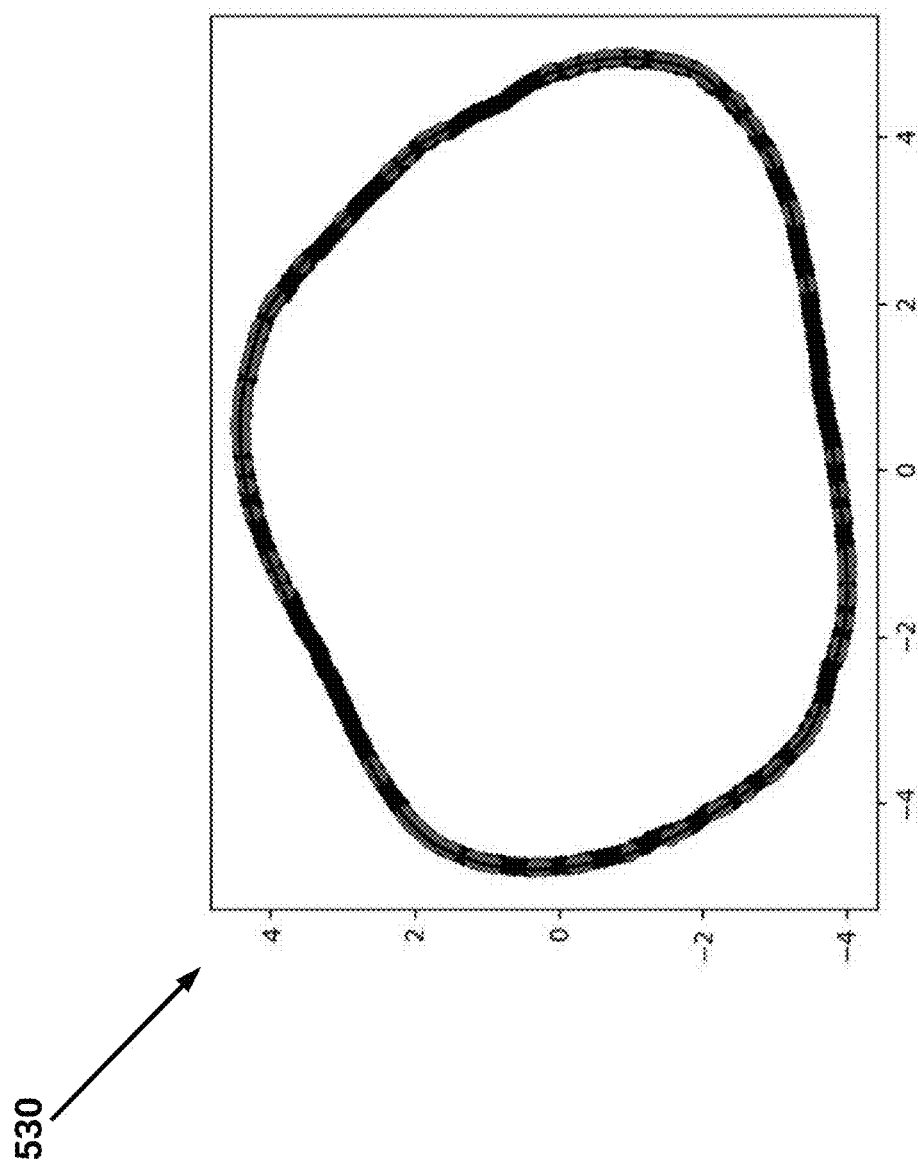
FIG. 5D illustrates example refined output with example confidence information.

FIG. 5D illustrates example refined output 530 with example confidence information. The refined output 530 may be similar to the representation 104 described in FIG.

1A. For example, a confidence associated with points forming the estimated margin may be graphically depicted. As an example, each point may be assigned a color based on the associated confidence (e.g., a first color or color intensity may represent a point with a relatively low confidence value, while a second color or color intensity may represent a point with a relatively high confidence value). In some embodiments, an intensity of the color along a range of intensity values may be used, such that the user can visually determine the relative confidence of each point relative to one another along a spectrum or range. In other embodiments, two colors may be used, where one color represents points having a confidence value meeting a threshold, and the other color represents points having a confidence value that fails to meet the confidence threshold.

Figure 6:
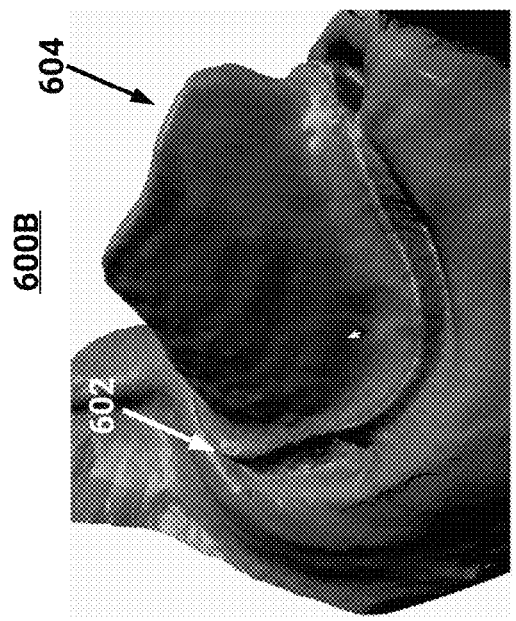
FIG. 6 illustrates examples of an estimated margin positioned on an intraoral scan.
Figure 6:
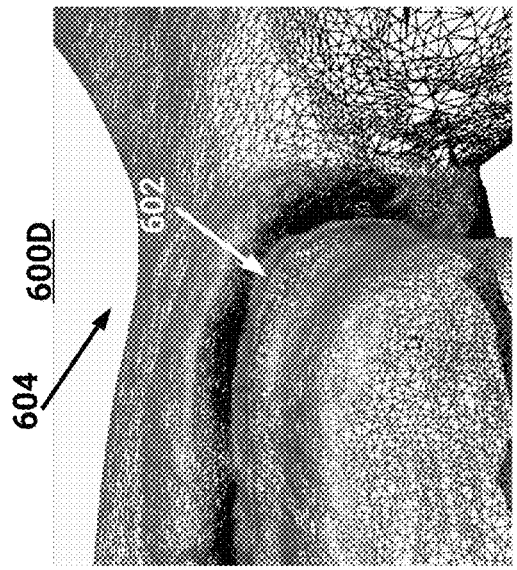
Figure 6:
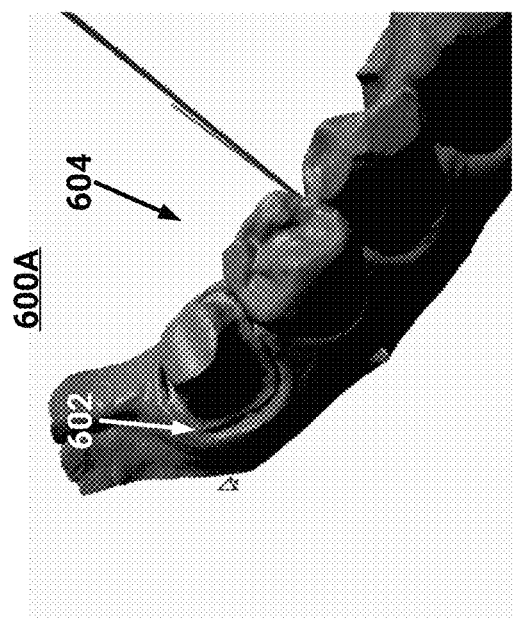
Figure 6:
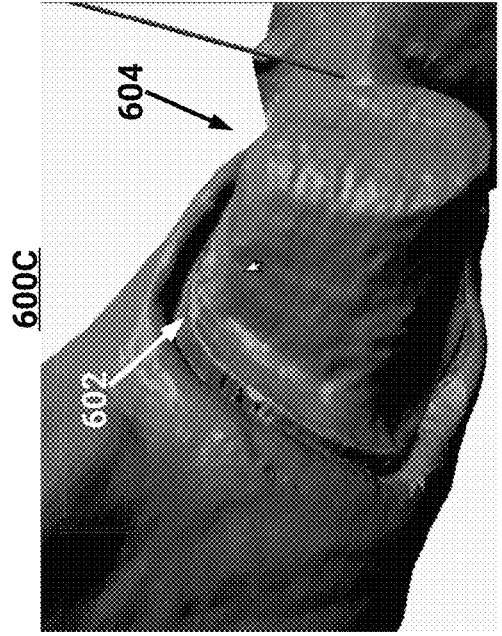

FIG. 6 illustrates example views 600A-600D of an estimated margin 602 positioned on an intraoral scan 604. The estimated margin may optionally be presented on the intraoral scan, for example as a three-dimensional representation. This three-dimensional representation may advantageously be included in a user interface accessible to a user. Via user input, the user may rotate, scale, and otherwise adjust the estimated margin. Example user input may include use of a mouse, keyboard, a touch-screen display, verbal commands, and so on. While a user interface presented via a user device is described herein, it may be appreciated that the estimated margin may be presented as virtual or augmented reality content for the user to view.

For example, a first view 600A includes a zoomed out view of the intraoral scan 604. In this example, a user may view a large portion of the estimated margin 602. Thus, the user may identify whether the estimated margin 602 adheres to a correct estimation. As another example, a second view 600B includes a closer view of the intraoral scan 604. In this example, the user may view more details associated with placement of the estimated margin. As another example, a third view 600C includes a rotation of the intraoral scan 604. For example, a user may have provided user input to cause a rotation of the scan 604. Thus, a different vantage point of the estimated margin 602 may be seen.

A fourth view 600D is also illustrated. This fourth view 600D is zoomed further into the intraoral scan 604, such that underlying points or portions of a mesh may be viewed. In the illustrated example, a mesh is shown which includes a multitude of connecting triangles or polygons. In some embodiments, a point cloud may be converted into a mesh for this fourth view 600D. For example, and as described above, techniques to generate a mesh from a point cloud may be used. Thus, for ease of viewing, the fourth view 600D may illustrate connecting triangles or polygons.

Example User Interfaces

FIG. 7A illustrates an example user interface 700 presenting an example estimated margin 710. The user interface 700 may be an example of a user interface generated by a user device. For example, the user interface 700 may be rendered by a browser executing on the user device. In this example, the user interface 700 may represent a front-end of a web application associated with the margin determination system 100. As another example, the user interface 700 may be rendered by an application executing on the user device. For example, the application may be obtained from an application store. The margin determination system 100 may provide information for presentation in the user interface 700.

In the illustrated example, a user of the user interface 700 can provide an intraoral scan for analysis by the margin determination system 100. For example, the user may interact with portion 702 to select a scan which may be stored in local or network storage. A representation of the intraoral scan 702 may be presented in the user interface 700. In this way, the user may ensure the correct scan was selected.

In response, the user interface 700 may be updated to present an estimated margin 710 based on the selected scan. For example, a two-dimensional representation 712 is included. As described in FIG. 5D, the two-dimensional representation 712 may graphically depict confidence information associated with the estimated margin. As another example, a three-dimensional representation 714 is included. As described in FIG. 6, the user of the user interface 700 can manipulate the representation 714 via user input. For example, the user may rotate the representation, zoom into or out of the representation, and so on.

While not illustrated, in some embodiments the user interface 700 may present quality score information associated with the estimated margin. For example, an overall margin quality may be presented. As another example, particular values of metrics used to determine the margin quality may be presented. Optionally, the values may be assigned colors or labels indicating a degree to which they positively or negative impacted the margin quality.

FIG. 7B illustrates another example of the user interface 700. In FIG. 7B, a user device 110 is shown as presenting the user interface 700. The user device 110 may additionally be in communication with a system or device usable to, at least in part, fabricate a prosthetic. Upon review of the estimated margin 702 in the user interface 700, the user of the user interface 700 may optionally cause a prosthetic fabrication system 720 to receive margin information 722. The margin information 722 may optionally be packaged, or of a form, associated with the system 720. For example, the system 720 may represent a three-dimensional printer. In this example, the margin information 722 may include information identifying a geometry of the estimated margin. The margin information 722 may optionally include a geometry associated with a prosthetic being fabricated. Thus, the system 720 may fabricate the prosthetic while ensuring that the estimated margin is followed.

Other Embodiments

Figure 8:
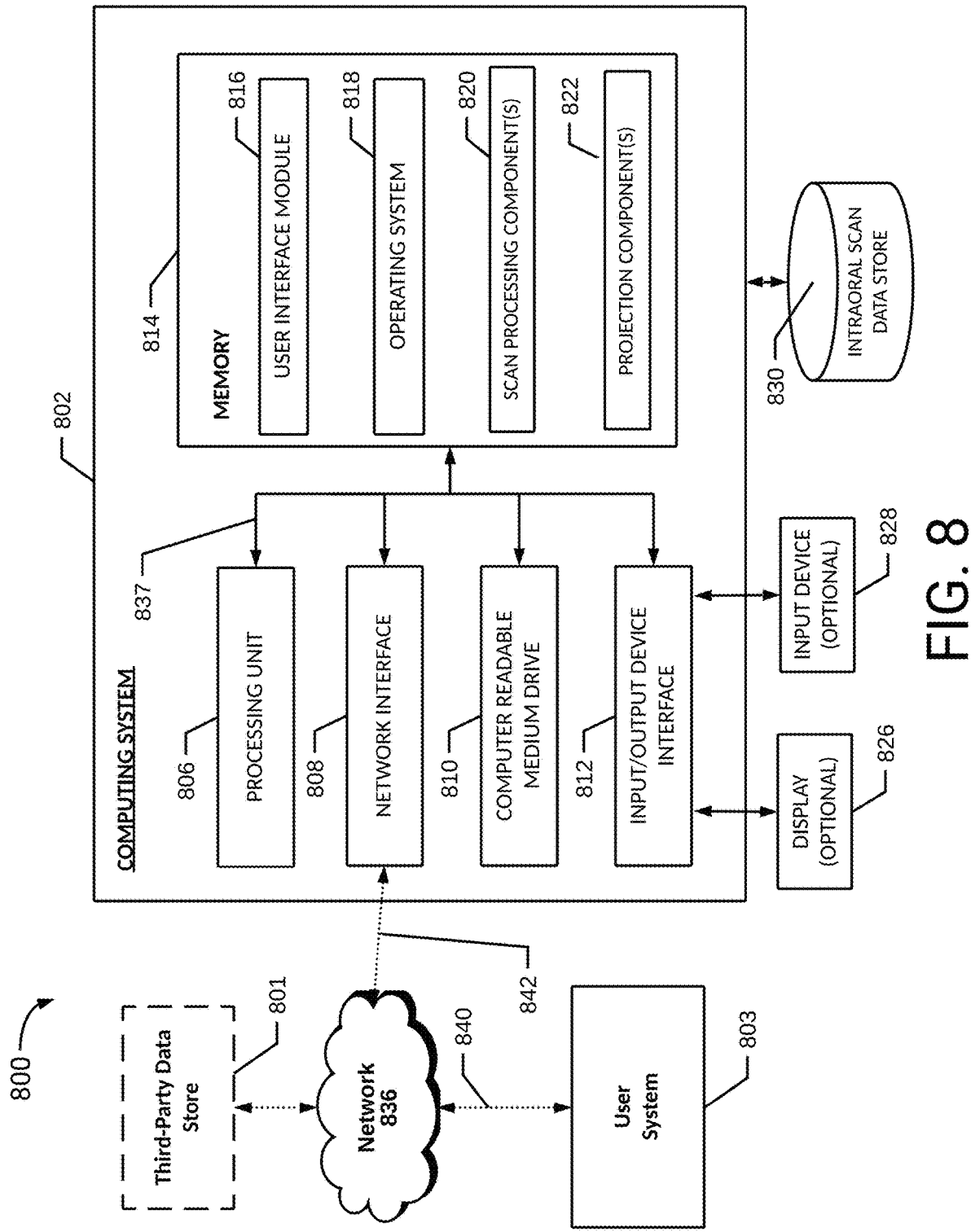
FIG. 8 illustrates a general architecture of a computing environment, according to some embodiments.

FIG. 8 illustrates a general architecture of a computing environment 800, according to some embodiments. As depicted in FIG. 8, the computing environment 800 may include a computing system 802. The general architecture of the computing system 802 may include an arrangement of computer hardware and software components used to implement aspects of the present disclosure. The computing system 802 may include many more (or fewer) elements than those shown in FIG. 8. It is not necessary, however, that all of these generally conventional elements be shown in order to provide an enabling disclosure. In some embodiments, the computing system 802 may be an example of what is referred to as the margin determination system above, though a medical provider system described above may include one or more similar components, in some embodiments.

As illustrated, the computing system 802 includes a processing unit 806, a network interface 808, a computer readable medium drive 810, an input/output device interface 812, an optional display 826, and an optional input device 828, all of which may communicate with one another by way of a communication bus 837. The processing unit 806 may communicate to and from memory 814 and may provide output information for the optional display 826 via the input/output device interface 812. The input/output device interface 812 may also accept input from the optional input device 828, such as a keyboard, mouse, digital pen, microphone, touch screen, gesture recognition system, voice recognition system, or other input device known in the art.

The memory 814 may contain computer program instructions (grouped as modules or components in some embodiments) that the processing unit 806 may execute in order to implement one or more embodiments described herein. The memory 814 may generally include RAM, ROM and/or other persistent, auxiliary or non-transitory computer-readable media. The memory 814 may store an operating system 818 that provides computer program instructions for use by the processing unit 806 in the general administration and operation of the computing system 802. The memory 814 may further include computer program instructions and other information for implementing aspects of the present disclosure. For example, in one embodiment, the memory 814 may include a user interface module 816 that generates user interfaces (and/or instructions therefor) for display upon a computing system, e.g., via a navigation interface such as a browser or application installed on the computing system 802 or the client computing system 803.

In some embodiments, the memory 814 may include one or more scan processing components 820 and projection components 822, which may be executed by the processing unit 806 to perform operations according to various embodiments described herein. The modules 820 and/or 822 may access the intraoral scan data store 830 in order to retrieve and analyze intraoral scans and generate graphical representations of estimated margins as described herein. The data store may be part of the computing system 802, remote from the computing system 802, and/or may be a network-based service.

In some embodiments, the network interface 808 may provide connectivity to one or more networks or computing systems, and the processing unit 806 may receive information and instructions from other computing systems or services via one or more networks. In the example illustrated in FIG. 8, the network interface 808 may be in communication with a client or user computing system 803 via the network 836, such as the Internet. In particular, the computing system 802 may establish a communication link 842 with a network 836 (e.g., using known protocols) in order to send communications to the computing system 803 over the network 836. Similarly, the computing system 803 may send communications to the computing system 802 over the network 836 via a wired or wireless communication link 840. In some embodiments, the computing system 802 may additionally communicate via the network 836 with an optional third-party data store or data service 801, which may be used by the computing system 802 to retrieve remotely stored intraoral scans or other files.

Those skilled in the art will recognize that the computing systems 802 and 803 may be any of a number of computing systems including, but not limited to, a laptop, a personal computer, a mobile phone, a smartphone, a tablet computer, another wireless device, a set-top or other television box, one or more servers, and the like. The client computing system 803 may include similar hardware to that illustrated as being included in computing system 802, such as a display, processing unit, network interface, memory, operating system, etc. In some embodiments, the client computing system 803 may be a medical provider system as described above or may be utilized by a dentist marking images or scans for machine learning training purposes or by dental lab personnel.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more general purpose computers or processors. The code modules may be stored in any type of non-transitory computer-readable medium or other computer storage device. Some or all the methods may alternatively be embodied in specialized computer hardware. In addition, the components referred to herein may be implemented in hardware, software, firmware or a combination thereof.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

It should be emphasized that many variations and modifications may be made to the above-described embodiments, the elements of which are to be understood as being among other acceptable examples. All such modifications and variations are intended to be included herein within the scope of this disclosure.

What is claimed is:

1. A computer system comprising:
   memory; and
   a processor in communication with the memory and configured with processor-executable instructions to perform operations comprising:
      receiving, via an application programming interface (API), a request including an intraoral scan of a portion of a mouth, the portion of the mouth being prepared by a dental professional to receive a prosthetic at a margin created via adjustment of a tooth, wherein the intraoral scan is a point cloud comprising a plurality of points, and wherein each of the points is associated with a three-dimensional coordinate;
      identifying, based on the intraoral scan, a prepared region depicting the tooth;
      generating a voxelized representation of points included in a portion of the point cloud associated with the prepared region, the voxelized representation including a plurality of voxels each comprising a respective subset of the points included in the portion;
      determining information identifying an estimated margin based on the voxelized representation via computing a forward pass of a machine learning model; and
      generating, via the API, a response comprising the determined information, wherein the determined information is usable to fabricate the prosthetic according to the estimated margin.

2. The computer system of claim 1, wherein identifying the prepared region is based on at least one of (a) a particular machine learning model trained to label the prepared region, or (b) density information associated with the point cloud.

3. The computer system of claim 1, wherein generating the voxelized representation comprises determining intersections of a plurality of bounding boxes with the portion of the point cloud, each bounding box representing a voxel of the voxelized representation.

4. The computer system of claim 1, wherein the machine learning model assigns values to each point indicating a confidence associated with the point forming the estimated margin.

5. The computer system of claim 4, wherein the operations further comprise:
   determining a centroid associated with first points forming the estimated margin, the first points representing a cross-section of the estimated margin; and
   refining the estimated margin based on filtering one or more of the first points which are greater than a threshold distance from the centroid.

6. The computer system of claim 1, wherein the information identifying the estimated margin comprises three-dimensional coordinates of points forming the estimated margin.

7. The computer system of claim 1, wherein the operations further comprise:
   generating, based on the information identifying the estimated margin, a three-dimensional representation of the estimated margin, wherein the three-dimensional representation is positioned on the received intraoral scan; and updating a user interface presented via a user device, the user interface enabling three-dimensional manipulation of the intraoral scan.

8. A method implemented by a system of one or more computers, the method comprising:

receiving, from a user device, a request including an intraoral scan of a portion of a mouth, the intraoral scan depicting a margin created via adjustment of a tooth;

identifying, based on the intraoral scan, a prepared region depicting the tooth;

generating a representation of the prepared region of the intraoral scan usable as input to a machine learning model, wherein the representation comprises structured data associated with a point cloud or mesh of the intraoral scan;

determining information identifying an estimated margin based on the representation via computing a forward pass of the machine learning model; and generating, for transmission to the user device, a response comprising the determined information, wherein the determined information is usable to fabricate a prosthetic according to the estimated margin.

9. The method of claim 8, wherein the intraoral scan comprises the point cloud or a mesh.

10. The method of claim 9, wherein the intraoral scan comprises the point cloud, and wherein generating the representation comprises:

generating a voxelized representation of points included in a portion of the point cloud associated with the prepared region, the voxelized representation including a plurality of voxels each comprising a respective subset of the points included in the portion.

11. The method of claim 8, further comprising:

determining quality score information associated with the estimated margin, the quality score information reflected, at least, a margin score indicative of an accuracy associated with the estimated margin, wherein at least a portion of the quality score information is included in the response.

12. The method of claim 11, wherein determining the margin score is based on a plurality of metrics, the metrics being based on curvature information associated with the estimated margin, and wherein determining the curvature information comprises:

determining a center associated with the estimated margin line; and traversing the determined center, and while traversing the center, computing variance of curvature and/or moments of curvature associated with the estimated margin.

13. The method of claim 8, further comprising:

refining the estimated margin, wherein refining comprises filtering points or portions of a mesh forming the estimated margin.

14. The method of claim 8, wherein the information identifying the estimated margin is usable to generate one or more graphical representations of the estimated margin.

15. Non-transitory computer storage media storing instructions that when executed by a system of one or more computers, cause the one or more computers to perform operations comprising:

obtaining an intraoral scan of a portion of a mouth, the intraoral scan depicting a margin created via adjustment of a tooth;

identifying, based on the intraoral scan, a prepared region depicting the tooth;

generating a representation of the prepared region of the intraoral scan usable as input to a machine learning model, wherein the representation comprises structured data associated with a point cloud or mesh;

determining information identifying an estimated margin based on the representation via computing a forward pass of the machine learning model; and generating a data structure usable as input for a dental prosthetic fabrication process, wherein the data structure comprises the determined information.

16. The computer storage media of claim 15, wherein the intraoral scan comprises the point cloud or a mesh.

17. The computer storage media of claim 16, wherein the intraoral scan comprises a point cloud, and wherein generating the representation comprises:

generating a voxelized representation of points included in a portion of the point cloud associated with the prepared region, the voxelized representation including a plurality of voxels each comprising a respective subset of the points included in the portion.

18. The computer storage media of claim 15, wherein the operations further comprise:

determining quality score information associated with the estimated margin, the quality score information reflecting, at least, a margin score indicative of an accuracy associated with the estimated margin, wherein at least a portion of the quality score information is included in the response.

19. The computer storage media of claim 15, wherein the operations further comprise:

refining the estimated margin, wherein refining comprises filtering points or portions of a mesh forming the estimated margin.

20. The computer storage media of claim 15, wherein the information identifying the estimated margin is usable to generate one or more graphical representations of the estimated margin.

* * * * *